(12) United States Patent
Ross

(10) Patent No.: US 10,806,541 B2
(45) Date of Patent: Oct. 20, 2020

(54) SCANNABLE OPTICAL IDENTIFIER FOR USE WITH IMPLANTABLE MEDICAL DEVICES

(71) Applicant: Adam Ross, Brooklyn, NY (US)

(72) Inventor: Adam Ross, Brooklyn, NY (US)

(*) Notice: Subject to any disclaimer, the term of this patent is extended or adjusted under 35 U.S.C. 154(b) by 450 days.

(21) Appl. No.: 15/617,027

(22) Filed: Jun. 8, 2017

(65) Prior Publication Data
US 2017/0354477 A1    Dec. 14, 2017

Related U.S. Application Data

(60) Provisional application No. 62/347,242, filed on Jun. 8, 2016, provisional application No. 62/393,981, filed on Sep. 13, 2016.

(51) Int. Cl.
| | | |
|---|---|---|
| *A61B 90/90* | (2016.01) | |
| *A61B 90/94* | (2016.01) | |
| *A61B 90/96* | (2016.01) | |
| *A61B 6/00* | (2006.01) | |
| *A61B 6/12* | (2006.01) | |
| *A61N 1/372* | (2006.01) | |
| *A61B 90/00* | (2016.01) | |

(52) U.S. Cl.
CPC ............... *A61B 90/96* (2016.02); *A61B 6/12* (2013.01); *A61B 6/44* (2013.01); *A61B 6/4429* (2013.01); *A61B 6/4452* (2013.01); *A61B 6/52* (2013.01); *A61B 6/5205* (2013.01); *A61B 6/5211* (2013.01); *A61B 6/5217* (2013.01); *A61B 90/90* (2016.02); *A61N 1/37217* (2013.01); *A61B 2090/3966* (2016.02); *A61M 2205/04* (2013.01); *A61M 2205/051* (2013.01); *A61M 2205/32* (2013.01); *A61M 2205/6063* (2013.01); *A61M 2205/6072* (2013.01)

(58) Field of Classification Search
CPC .......... A61B 6/12; A61B 6/52; A61B 6/5205; A61B 6/5211; A61B 6/5217; A61B 90/30; A61B 2090/3937; A61B 2090/3966; A61B 2090/3983; A61B 90/39; A61B 90/90; A61B 90/94; A61B 90/96; A61B 6/44; A61B 6/4429; A61B 6/4452; A61M 2205/04; A61M 2205/051; A61M 2205/32; A61M 2205/6063; A61M 2205/6072
USPC .......................................... 378/62, 162, 165
See application file for complete search history.

(56) References Cited

U.S. PATENT DOCUMENTS

| | | | | |
|---|---|---|---|---|
| 7,429,920 B2 * | 9/2008 | Smythe | ............... | A61B 5/0031 340/539.12 |
| 7,785,302 B2 * | 8/2010 | Powers | ............ | A61M 39/0208 |
| 7,831,096 B2 * | 11/2010 | Williamson, Jr. | ...... | G06T 15/00 382/195 |

(Continued)

OTHER PUBLICATIONS

Van Haute et al., Performance analysis of multiple Indoor Positioning Systems in a healthcare environment, International Journal of Health Geographics, 2016, vol. 5, No. 7, pp. 1-15.

*Primary Examiner* — Allen C. Ho
(74) *Attorney, Agent, or Firm* — Pandiscio & Pandiscio

(57) ABSTRACT

Apparatus for identifying a patient, said apparatus comprising: a medical device for implantation into the patient; an optical identifier affixed to the medical device; wherein at least a portion of the optical identifier is radiopaque, whereby to generate a scannable X-ray image of the optical identifier when the medical device is imaged using X-ray.

24 Claims, 4 Drawing Sheets

(56) References Cited

U.S. PATENT DOCUMENTS

| | | | | |
|---|---|---|---|---|
| 7,947,022 | B2* | 5/2011 | Amin | A61M 39/0208 604/288.02 |
| 8,029,482 | B2* | 10/2011 | Maniar | A61M 39/0208 604/288.02 |
| 8,160,328 | B2* | 4/2012 | Goetz | A61N 1/0551 382/128 |
| 8,246,671 | B2* | 8/2012 | Khairkhahan | A61B 17/0057 623/1.11 |
| 8,339,262 | B2* | 12/2012 | Pless | G06F 21/35 128/903 |
| 8,812,125 | B2* | 8/2014 | Kaula | A61N 1/37247 607/59 |
| 8,945,090 | B2* | 2/2015 | Rassatt | A61N 1/05 600/372 |
| 8,960,555 | B1* | 2/2015 | Walton, III | G06K 19/06037 235/487 |
| 8,989,843 | B2* | 3/2015 | Chien | A61B 6/12 600/424 |
| 9,044,173 | B2* | 6/2015 | Crouch | G06T 7/0014 |
| 9,227,024 | B2* | 1/2016 | Deutsch | A61M 5/5086 |
| 9,265,912 | B2* | 2/2016 | Draper | G06Q 50/22 |
| 9,314,219 | B2* | 4/2016 | Keall | A61B 6/5217 |
| 9,317,920 | B2* | 4/2016 | Gluncic | G06K 9/00 |
| 9,320,569 | B2* | 4/2016 | Lloyd | A61B 90/36 |
| 9,446,264 | B2* | 9/2016 | Sawkey | A61N 5/1068 |
| 9,529,969 | B2* | 12/2016 | Brennan | G16H 10/60 |
| 9,700,234 | B2* | 7/2017 | Mickle | A61B 5/4851 |
| 9,727,548 | B2* | 8/2017 | Watanabe | G06F 40/205 |
| 9,757,200 | B2* | 9/2017 | Magee | A61M 25/00 |
| 9,792,682 | B2* | 10/2017 | Gluncic | A61B 6/12 |
| 9,980,082 | B2* | 5/2018 | Nhu | H04W 4/70 |
| 10,046,167 | B2* | 8/2018 | Schmidt | A61N 1/375 |
| 10,071,174 | B2* | 9/2018 | Goforth | A61L 31/18 |
| 10,293,178 | B2* | 5/2019 | De Vries | A61B 90/30 |
| 10,357,183 | B2* | 7/2019 | Marentis | A61B 6/12 |
| 10,431,330 | B2* | 10/2019 | Lal | G16H 10/60 |
| 10,433,911 | B2* | 10/2019 | Wang | A61B 90/30 |
| 2014/0263674 | A1 | 9/2014 | Cerveny | |
| 2016/0174022 | A1 | 6/2016 | Nhu | |

* cited by examiner

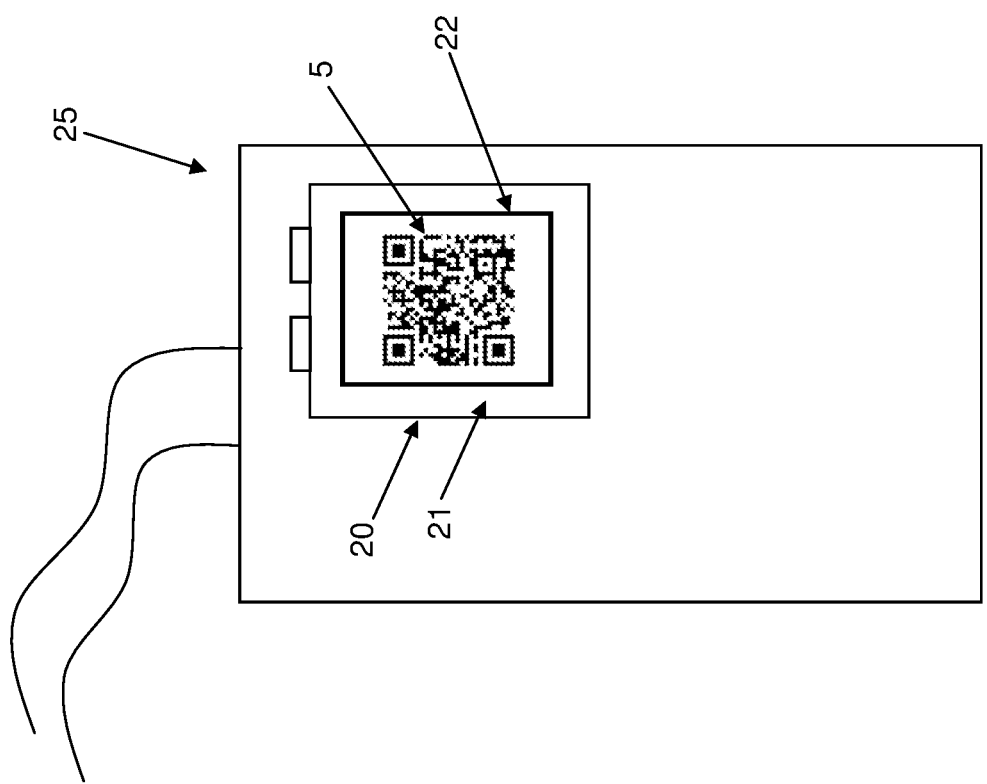

SCANNABLE OPTICAL IDENTIFIER FOR USE WITH IMPLANTABLE MEDICAL DEVICES

REFERENCE TO PENDING PRIOR PATENT APPLICATIONS

This patent application claims benefit of:

(i) prior U.S. Provisional Patent Application Ser. No. 62/347,242, filed Jun. 8, 2016 by Adam Ross for INTEGRATION OF PATIENT SPECIFIC RADIOPAQUE SCANNABLE CODE WITHIN CARDIAC IMPLANTABLE ELECTRONIC DEVICES (CIEDS); and (ii) prior U.S. Provisional Patent Application Ser. No. 62/393,981, filed Sep. 13, 2016 by Adam Ross for INTEGRATION OF PATIENT SPECIFIC RADIOPAQUE SCANNABLE CODE WITHIN CARDIAC IMPLANTABLE ELECTRONIC DEVICES (CIEDS).

The two (2) above-identified patent applications are hereby incorporated herein by reference.

FIELD OF THE INVENTION

This invention relates to implantable medical devices in general, and more particularly to novel optical identifiers applied to implantable medical devices which may be visualized during scanning and used to identify a medical device and/or a patient and/or to access a medical record.

BACKGROUND OF THE INVENTION

Implantable medical devices are often marked with alphanumeric identifiers (e.g., lot numbers, serial numbers, etc.). Such identifiers are commonly used to identify and/or track a medical device (e.g., during manufacture, shipping, use, etc.), and are typically noted in a patient's medical record, so that in the event of a medical device malfunction, recall, revision surgery, etc., there is a record of the particular implantable medical device which has been implanted into the patient. Inasmuch as the implantable medical device is typically implanted into the patient's body (and is, therefore, generally inaccessible and not directly viewable after being implanted), a healthcare provider typically requires either access to the patient's medical record, or direct visual access to the implanted medical device (e.g., via an incision) in order to know the identifier on a particular implanted medical device.

Alternatively, and/or additionally, an alphanumeric identifier on an implantable medical device may be replaced by (or supplemented by) a radio frequency identification (RFID) "tag". By way of example but not limitation, more than 400,000 cardiac implantable electronic devices (CIEDs) are implanted into patients every year in the United States. When a patient with one of these devices presents to their cardiologist (or to an emergency department), any cardiac implantable electronic devices (CIEDs) having an RFID chip may then be identified and analyzed via the RFID chip which is embedded within them (and which can communicate with a reader device external to the patient's body).

One limitation associated with the current RFID technology is the requirement of a reader device (commonly referred to as a "programmer"), which is typically placed on the patient's skin over the cardiac implantable electronic device (CIED) and which communicates with the RFID "tag" presented by the cardiac implantable electronic device. The programmer can provide information about the cardiac implantable electronic device itself (i.e., information received from the RFID tag associated with the cardiac implantable electronic device), but the data provided by the RFID tag is limited in nature and does not provide specific information about the patient which can be critical to patient care. Put another way, where an RFID tag is provided to identify the implant, it typically requires a specialized electronic reader (i.e., a "programmer") to read the RFID tag, and event then the RFID tag does not provide patient-specific information (e.g., the patient's medical record). In addition, a particular programmer may be device-specific, so it may be necessary to keep multiple programmers on hand.

If medical records are lost, or if the patient is not able to provide identifying information (e.g., if the patient is unconscious or non-responsive after an accident or other medical event), it would be desirable for a healthcare provider to be able to identify an implanted medical device, and/or the patient, and/or patient-specific information, from identifying information provided on the implanted medical device (but not readily viewable since the implanted medical device is disposed within the patient's body), without the need for direct visual access to the implanted medical device. In addition, it would be desirable to be able to read the information on an implanted medical device without the need for implant/device-specific electronic "programmers".

Thus there is a need for a new and improved optical identifier that can be used to identify an implant and/or the patient and/or patient-specific information without requiring direct visual access to the implant and without requiring specialized programmers or device-specific equipment.

SUMMARY OF THE INVENTION

These and other objects of the present invention are addressed by the provision and use of a novel optical identifier which can be visualized using common X-ray equipment so as to generate a scannable X-ray image which can then be scanned using a common hand-held device (e.g., a smartphone, PDA, etc.), whereby to provide implant-specific and/or patient-specific information to a healthcare provider.

In one preferred form of the invention, there is provided apparatus for identifying a patient, said apparatus comprising:

a medical device for implantation into the patient;

an optical identifier affixed to said device;

wherein at least a portion of said optical identifier is radiopaque, whereby to generate a scannable X-ray image of said optical identifier when said medical device is imaged using X-ray.

In another preferred form of the invention, there is provided a method for identifying a patient using an implanted medical device, said method comprising:

providing an implanted medical device comprising:

a medical device for implantation into the patient;

an optical identifier affixed to said device;

wherein at least a portion of said optical identifier is radiopaque, whereby to generate a scannable X-ray image of said optical identifier when said medical device is imaged using X-ray;

using an X-ray source to scan said implanted medical device, whereby to generate a scannable X-ray image of said optical identifier; and using a scanner to scan said scannable X-ray image, whereby to scan said optical identifier;

wherein scanning said optical identifier produces information which can link said radiopaque optical identifier to a database, and further wherein the patient can be identified by looking up said information in said database.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 1A is a schematic view showing another novel optical identifier formed in accordance with the present invention being applied to the battery of an implantable medical device which is implanted into a patient;

DETAILED DESCRIPTION OF THE PREFERRED EMBODIMENTS

The present invention comprises the provision and use of a novel optical identifier which can be visualized using common X-ray equipment so as to generate a scannable X-ray image that can be scanned using a common hand-held device (e.g., a smartphone, PDA, etc.), whereby to provide implant-specific and/or patient-specific information to a healthcare provider.

Figure 1B:
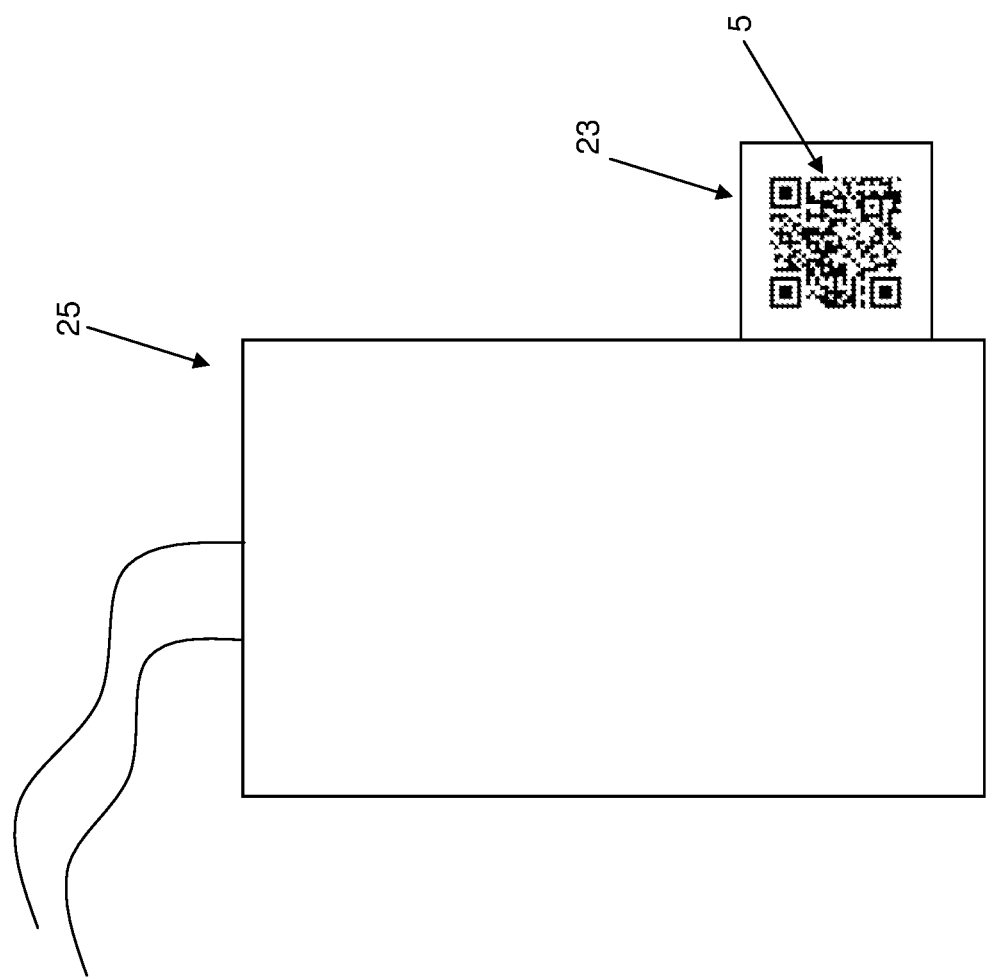
FIG. 1B is a schematic view showing another novel optical identifier formed in accordance with the present invention being applied to a flag on an implantable medical device which is implanted into a patient.

Looking first at FIG. 1, there is shown a novel optical identifier 5 which may be applied to an implantable medical device. Optical identifier 5 preferably comprises an optically-scannable "code" comprising regions of radiopaque material 10 (e.g., the "uncolored" regions of a QR code) and regions of radio-transmissive material 15 (e.g., the "black" regions of a QR code) as the QR code appears on an X-ray image, as will hereinafter be discussed in further detail. In one preferred form of the invention, radiopaque material 10 comprises a 3D printed metal such as gold or tantalum.

For purposes of clarity, optical identifier 5 will hereinafter sometimes be referred to as a Quick Reference code, or "QR code", however, it should be appreciated that substantially any optically-scannable identifier may be used with the present invention, as will be apparent to those skilled in the art in view of the present disclosure. By way of example but not limitation, optical identifier 5 may comprise linear bar codes, Data Matrix codes, Quickmark codes, Beetagg codes, Microsoft Tag codes, Trillcode codes, Aztec codes, Shotcode codes, Portable Data Format (PDF) codes, etc.

Optical identifier 5 is preferably affixed onto (or printed onto, or stamped onto, or formed onto, etc.) an element 20 of an implantable medical device 25. Element 20 of implantable medical device 25 preferably comprises a portion of implantable medical device 25 having a substantially uniform opacity when imaged using X-rays, as will hereinafter be discussed in further detail. To this end, element 20 preferably comprises a single material, having a uniform thickness at the point where optical identifier 5 is affixed to element 20. In a preferred form of the present invention, element 20 is removable from implantable medical device 25. In one preferred form of the invention, element 20 of implantable medical device 25 comprises the battery 21 (see FIG. 1A) of a cardiac implantable electronic devices (CIED). Affixing optical identifier 5 to a battery 21 is desirable since the battery typically comprises a material having a substantially constant density, and thereby provides a substantially constant background for visualizing optical identifier 5 on an X-ray scan, as will hereinafter be discussed in further detail. In this form of the invention, optical identifier 5 is preferably printed onto a sticker (or other adhesive) 22 (see FIG. 1A) which is then affixed to the battery 21 of the implantable medical device 25 (i.e., to element 20 of implantable medical device 25). It will also be appreciated that it may be advantageous to affix optical identifier 5 to the battery 21 of an implantable medical device in order to allow an optical identifier 5 to be added to an implantable medical device which has previously lacked an optical identifier 5 (i.e., so that the optical identifier is provided to the implanted medical device when the battery is replaced).

Alternatively, if desired, optical identifier 5 may be affixed to a tag 23 (see FIG. 1B) which extends away from implantable medical device 25 (e.g., in the manner of a "flag" 23).

Implantable medical device 25 is implanted into a patient 30 such that optical identifier 5 lies beneath the skin of the patient (i.e., such that optical identifier 5 is not viewable to the naked eye).

Figure 2:
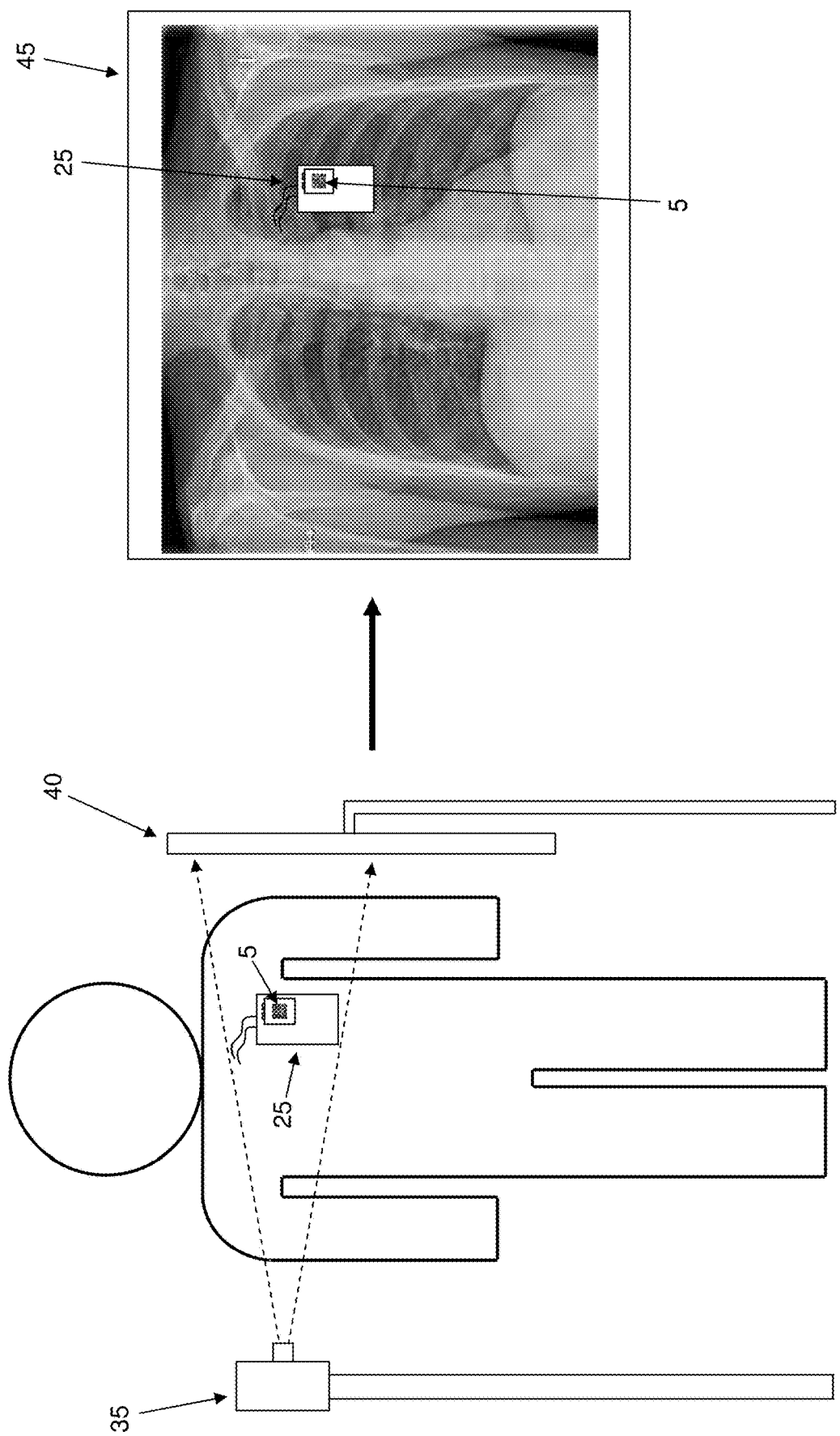
FIG. 2 is a schematic view showing how the novel optical identifier of FIG. 1 can be scanned so as to generate an X-ray image.

Looking next at FIG. 2, if a healthcare provider desires to visualize optical identifier 5 after implantable medical device 25 has been implanted into patient 30, an X-ray source 35 may be used to pass X-ray beams through patient 30 such that the X-ray beams are detected by a detector 40, whereby to generate an X-ray image 45. It will be appreciated that inasmuch as radiopaque material 10 blocks (or attenuates) the passage of X-rays through the regions of optical identifier 5 comprising radiopaque material 10, the portions of optical identifier 5 comprising radiopaque material 10 appear comparatively lighter (e.g., "uncolored") on X-ray image 45 than the portions of optical identifier 5 comprising radio-transmissive material 15 (which allows X-rays to pass through with less attenuation and therefore appears darker, e.g., "black" on X-ray image 45). As a result, optical identifier 5 can be easily readable on X-ray image 45 for scanning by a handheld scanner, as will hereinafter be discussed.

Figure 3:
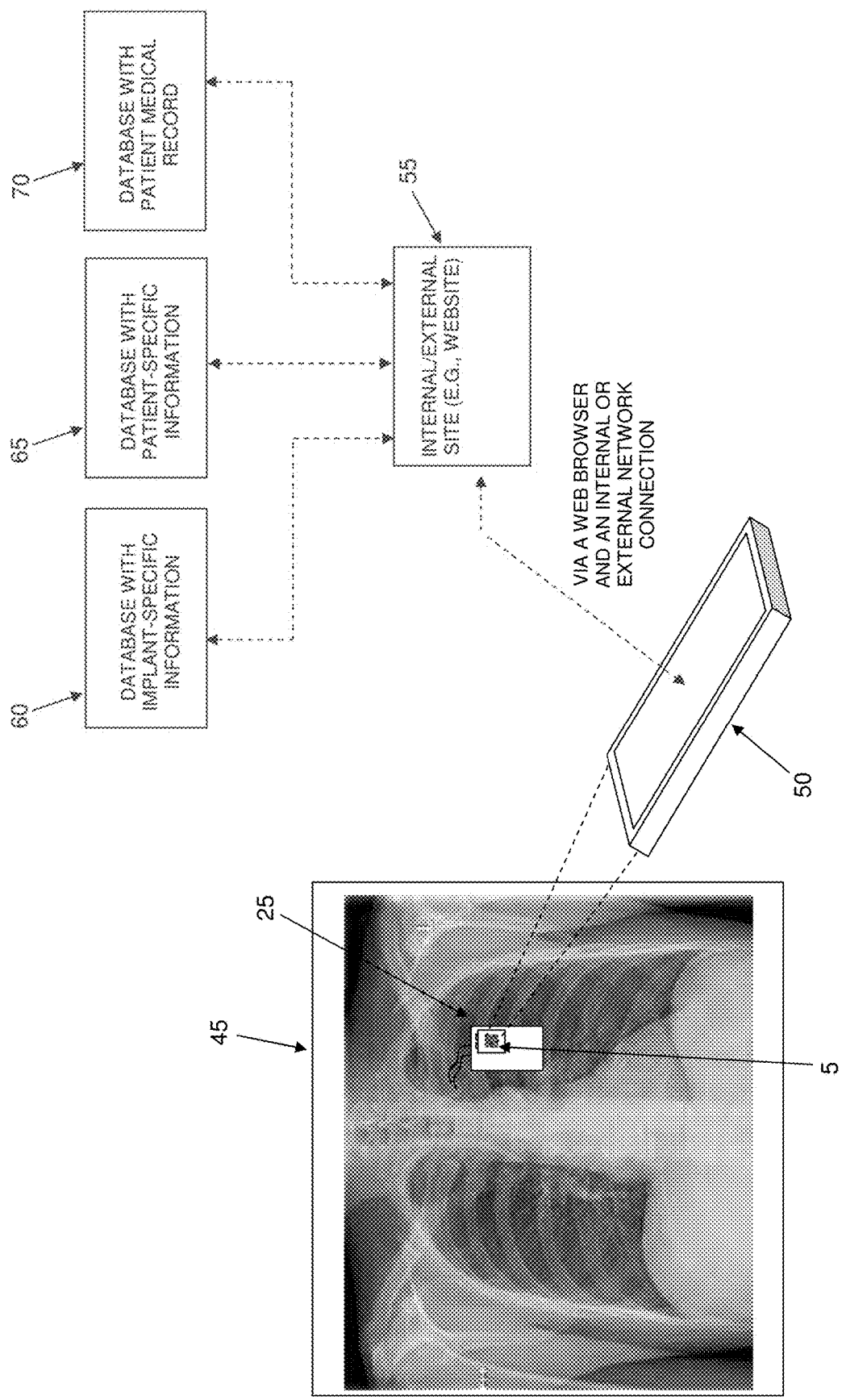
FIG. 3 is a schematic view showing how a handheld scanner may be used to scan the X-ray image of FIG. 2 so as to obtain implant-specific and/or patient-specific information.

After generating X-ray image 45, and looking now at FIG. 3, a healthcare provider can use a common handheld scanner 50 (e.g., a smartphone, a PDA, a barcode/QR code scanner, etc.) to scan the image of optical identifier 5 appearing on X-ray image 45. Alternatively, the optical identifier 5 can be digitally scanned (i.e., automatically, using a computer program).

Optical identifier 5 may be configured to contain information about implantable medical device 25 (e.g., a serial number, lot number, operating information, etc.) and/or optical identifier 5 may be configured to contain patient-specific information and/or link directly to a patient's medical record. By way of example but not limitation, optical identifier 5 may comprise a QR code which incorporates a universal resource locator (URL) which links to a secured website (e.g., which automatically re-directs handheld scanner 50 to an implant-specific and/or patient-specific URL that contains information about the implantable medical device 25 and/or the patient 30.

By way of example but not limitation, optical identifier 5 could link to an internal or external site (e.g., a website) 55 which could, in turn, link to one or more databases (e.g., a database 60 containing implant-specific data, a database 65 containing patient-specific data, a database 70 containing a patient medical record, etc). If desired, a patient 30 may be able to control access to information retained on external (or internal) site 55, e.g., via a password-protected URL.

In this way, optical identifier 5 can allow a healthcare provider to access implant information and/or critical patient information (e.g., allergies, medications, next of kin, baseline EKG, etc.) using only a common, widely-available X-ray equipment and a common, widely-available handheld scanner 50, thereby avoiding the need for direct physical access to implantable medical device 25 or device-specific electronic equipment (e.g., "programmers").

Optical identifier 5 may also be used to provide information which could be used to directly control the implantable medical device 25. By way of example but not limitation, optical identifier 5 could take the place of a traditional RFID within the implantable medical device 25, or optical identifier 5 could work in conjunction with the RFID as part of a two-factor authentication process. Alternatively and/or additionally, optical identifier 5 could serve as a backup to the RFID included with implantable medical device 25, should the RFID element of the implantable medical device became nonfunctional. In addition, if desired, an identical optical identifier 5 could be printed on a physical "implant card" that is carried by the patient 30, so as provide a backup in a situation where optical identifier 5 becomes unreadable on an X-ray image 45 due to interference/damage.

It will be appreciated that the provision and use of optical identifier 5 on an implantable medical device 25 provides numerous benefits in addition to those discussed above.

By way of example but not limitation, optical identifier 5 may be configured to link to a patient medical record, whereby to provide information to a healthcare provider even when the patient 30 is unconscious or non-responsive. For example, if a patient 30 has a cardiac implantable electronic device (CIED) such as a pacemaker, and the patient 30 collapses outside their home (e.g., while running, while at the gym, etc.), the patient 30 may be unable to provide any identifying information to emergency personnel. However, when a routine chest X-ray is thereafter performed (e.g., in the emergency department, as is typical for such a medical event), optical identifier 5 could be viewed on the X-ray image 45 generated, and thereafter scanned by a healthcare provider, so as to provide the healthcare provider with information about the cardiac implantable electronic device (CIED) or about the patient 30 (e.g., via a URL that links to a patient medical record), thereby facilitating treatment of the patient 30.

In addition, as discussed above, optical identifier 5 preferably comprises an optically-scannable pattern comprising a radiopaque material 10 and a radio-transmissive material 15. If desired, radiopaque material 10 may comprise an iridium-based ink or film which may be printed on implantable medical device 25. Iridium is a rare earth metal with many unique properties (e.g., it is extremely dense and has a high periodic number). These properties make it one of the most radiopaque elements and therefore an ideal candidate for use with medical imaging (e.g., X-ray imaging).

In addition to placing optical identifier 5 on implantable medical device 25, a second (e.g., identical or different) optical identifier (e.g., a iridium-based optical identifier) could be affixed to the outside of the patient's body, such that both optical identifier 5 and the second optical identifier can be visualized on the same X-ray image 45. By way of example but not limitation, the second optical identifier could comprise a patch or sticker worn by all patients who will be receiving multiple chest x-rays (e.g., patients on ventilators). The utility of this application would be as a post-test safeguard against inadvertent switching of X-ray films with another patient. The second optical identifier may be placed on the patient's back, outside the area of the ribcage so as not to interfere with the critical part of the film.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. An apparatus for identifying a patient comprising:
a medical device for implantation into the patient;
an optical identifier affixed to said medical device;
wherein at least a portion of said optical identifier is radiopaque, whereby to generate a scannable X-ray image of said optical identifier when said medical device is imaged using X-ray;
wherein said medical device comprises an element, and wherein said optical identifier is affixed to said element; and wherein said element comprises a battery.

2. The apparatus according to claim 1, wherein said optical identifier comprises a QR code.

3. The apparatus according to claim 1, wherein said optical identifier comprises a radiopaque material and a radio-transmissive material.

4. The apparatus according to claim 3, wherein said radiopaque material comprises at least one selected from the group consisting of tantalum, gold, and iridium.

5. The apparatus according to claim 1, wherein said optical identifier comprises a sticker which is affixed to said element.

6. The apparatus according to claim 1, wherein said medical device comprises a cardiac implantable electronic device (CIED).

7. The apparatus according to claim 1, wherein said element is removable.

8. An apparatus for identifying a patient comprising:
a medical device for implantation into the patient;
an optical identifier affixed to said medical device;
wherein at least a portion of said optical identifier is radiopaque, whereby to generate a scannable X-ray image of said optical identifier when said medical device is imaged using X-ray;
said medical device further comprising a flag, wherein said optical identifier is affixed to said flag.

9. The apparatus according to claim 8, wherein said optical identifier comprises a QR code.

10. The apparatus according to claim 8, wherein said optical identifier comprises a radiopaque material and a radio-transmissive material.

11. The apparatus according to claim 10, wherein said radiopaque material comprises at least one selected from the group consisting of tantalum, gold, and iridium.

12. The apparatus according to claim 8, wherein said optical identifier comprises a sticker which is affixed to said flag.

13. The apparatus according to claim 8, wherein said medical device comprises a cardiac implantable electronic device (CIED).

14. A method for identifying a patient using an implanted medical device, said method comprising:
providing an implanted medical device comprising:
a medical device for implantation into the patient;
an optical identifier affixed to said medical device;
wherein at least a portion of said optical identifier is radiopaque, whereby to generate a scannable X-ray image of said optical identifier when said medical device is imaged using X-ray;
using an X-ray source to scan said implanted medical device, whereby to generate a scannable X-ray image of said optical identifier; and
using a scanner to scan said scannable X-ray image, whereby to scan said optical identifier;
wherein scanning said optical identifier produces information which can link said optical identifier to a database, and wherein the patient can be identified by looking up said information in said database.

15. The method according to claim 14, wherein said optical identifier comprises a QR code.

16. The method according to claim 14, wherein said medical device comprises an element, and wherein said optical identifier is affixed to said element.

17. The method according to claim 16, wherein said element comprises a battery.

18. The method according to claim 16, wherein said element is removable.

19. The method according to claim 14, wherein said optical identifier comprises a radiopaque material and a radio-transmissive material.

20. The method according to claim 19, wherein said radiopaque material comprises at least one selected from the group consisting of tantalum, gold, and iridium.

21. The method according to claim 14, wherein said optical identifier comprises a sticker which is affixed to said medical device.

22. The method according to claim 14, wherein said optical identifier is affixed directly onto said medical device.

23. The method according to claim 14, wherein said medical device comprises a flag, and wherein said optical identifier is affixed to said flag.

24. The method according to claim 14, wherein said medical device comprises a cardiac implantable electronic device (CIED).

* * * * *